United States Patent
Mako

(10) Patent No.: US 9,968,325 B2
(45) Date of Patent: May 15, 2018

(54) RADIOGRAPHING APPARATUS, RADIOGRAPHING METHOD, AND PROGRAM

(71) Applicant: CANON KABUSHIKI KAISHA, Tokyo (JP)

(72) Inventor: Yuta Mako, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 104 days.

(21) Appl. No.: 15/146,156

(22) Filed: May 4, 2016

(65) Prior Publication Data
US 2016/0331340 A1 Nov. 17, 2016

(30) Foreign Application Priority Data
May 15, 2015 (JP) .................... 2015-100412

(51) Int. Cl.
*G06T 5/50* (2006.01)
*A61B 6/00* (2006.01)
*G06T 5/00* (2006.01)

(52) U.S. Cl.
CPC ............ *A61B 6/5258* (2013.01); *G06T 5/002* (2013.01); *G06T 5/50* (2013.01); *A61B 6/54* (2013.01); *G06T 2207/10116* (2013.01)

(58) Field of Classification Search
CPC .............. A61B 6/5258; A61B 6/54; G06T 2207/10116; G06T 5/002; G06T 5/50
See application file for complete search history.

(56) References Cited

U.S. PATENT DOCUMENTS

2009/0129659 A1* 5/2009 Deutschmann ...... A61N 5/1048
382/132

FOREIGN PATENT DOCUMENTS

JP 2003-190126 A 7/2003

* cited by examiner

*Primary Examiner* — Siamak Harandi
(74) *Attorney, Agent, or Firm* — Canon U.S.A., Inc. IP Division

(57) ABSTRACT

A radiographing apparatus includes a correction data acquiring unit configured to acquire, by image data obtained by photography in a predetermined photographing mode, offset correction data corresponding to the photographing mode, and a correction data update unit configured to update the offset correction data corresponding to the photographing mode by using a predetermined number of pieces of the image data, wherein the correction data update unit further is configured to adjust the number of pieces of the image data according to the photographing mode.

12 Claims, 5 Drawing Sheets

| MODE1 | MODE2 | MODE3 | MODE4 |
|---|---|---|---|
| $I1_n$ | $I2_n$ | $I3_n$ | $I4_n$ |

| MODE1 | MODE2 | MODE3 | MODE4 |
|---|---|---|---|
| $W1_m$ | $W2_m$ | $W3_m$ | $W4_m$ |
| $W1_n$ | $W2_n$ | $W3_n$ | $W4_n$ |

RADIOGRAPHING APPARATUS, RADIOGRAPHING METHOD, AND PROGRAM

BACKGROUND OF THE INVENTION

Field of the Invention

The present invention relates to a radiographing apparatus acquiring a radiation image based on a radiation detection signal which is transmitted through an object and detected, and particularly relates to a radiographing apparatus acquiring offset correction data.

Description of the Related Art

A radiation image captured by using radiations such as X-rays is widely used for disease diagnosis and the like. In recent years, a radiation image detector of a flat panel type (FPD) has been used for capturing a radiation image.

The radiation image detector converts radiations which are radiation for a certain accumulation time into an amount of electric charges and accumulates the electric charges in a capacitor. In a case where an electric charge which is unrelated to the radiation of the radiations exists in the radiation image detector at a time of photography, the electric charge is superimposed on the radiation image as noise, and causes deterioration of an image quality of the radiation image. For example, a dark current component due to an electric charge which is generated mainly by an influence of temperature causes noise in the radiation image detector.

In addition, at a time of photographing a radiation image, an electric charge of a dark current component increases in proportion to an accumulation time required for accumulating electric charges, and an image quality of the radiation image is thereby deteriorated. Accordingly, the radiation image detector generates an image (offset image), which is captured during a non-radiation time of radiations, as offset correction data and performs offset correction of the radiation image by using the offset correction data.

In Japanese Patent Laid-Open No. 2003-190126, when a radiation image detector has a plurality of photographing modes, the radiation image detector acquires offset correction data corresponding to each of the photographing modes before capturing a radiation image.

However, in a case where offset correction data is acquired in advance before photography of a radiation image detector, it takes so much time to acquire the offset correction data according to the number of photographing modes, and a waiting time from start of the radiation image detector to the photography becomes long. Moreover, since noise due to an influence of temperature or the like increases over time, update of the offset correction data becomes necessary, so that it takes so much time to update the offset correction data according to the number of photographing modes, and a waiting time from photography of a radiation image to next photography becomes long.

SUMMARY OF THE INVENTION

One aspect of the invention improves an image quality of a radiation image and shortens a waiting time of a radiographing apparatus.

According to an aspect of the present invention, a radiographing apparatus includes a correction data acquiring unit configured to acquire, by image data obtained by photography in a predetermined photographing mode, offset correction data corresponding to the photographing mode, and a correction data update unit configured to update the offset correction data corresponding to the photographing mode by using a predetermined number of pieces of the image data, wherein the correction data update unit further is configured to adjust the number of pieces of the image data according to the photographing mode.

Further features of the present invention will become apparent from the following description of exemplary embodiments with reference to the attached drawings.

DESCRIPTION OF THE EMBODIMENTS

First Exemplary Embodiment

Figure 1:
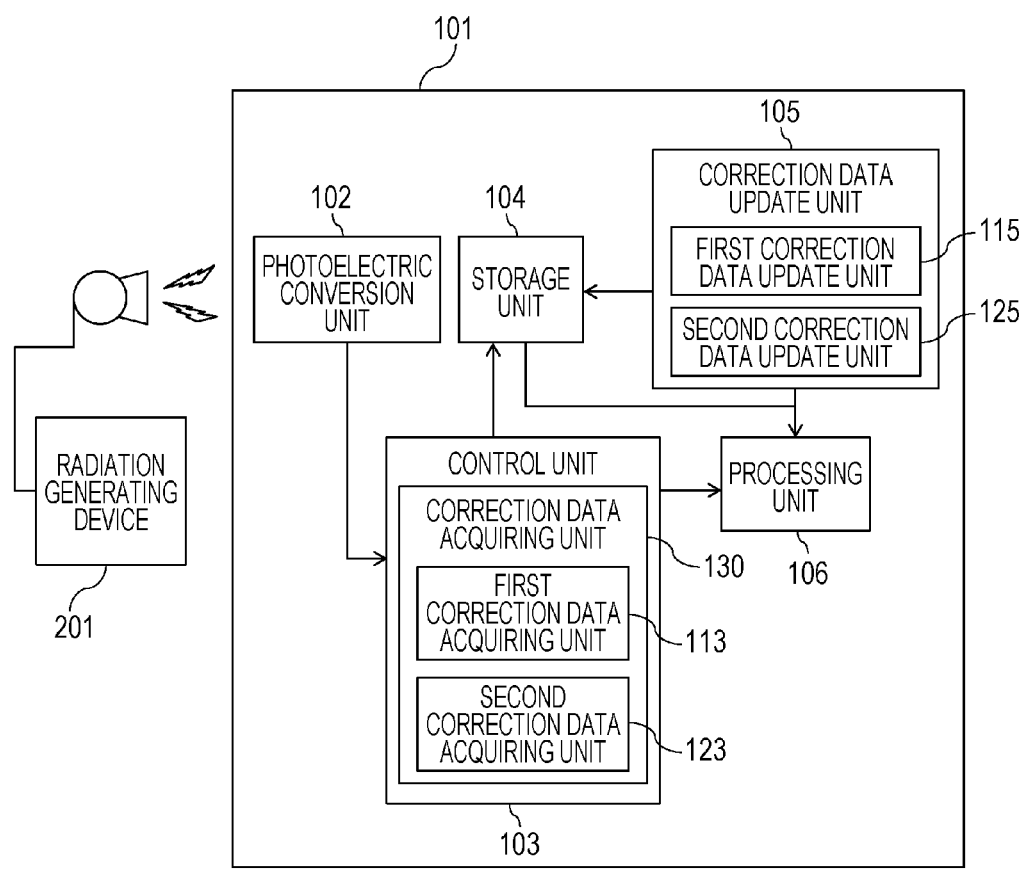
FIG. 1 is a schematic diagram illustrating one example of a schematic configuration of a radiographing apparatus according to a first exemplary embodiment.

Hereinafter, one example of a first exemplary embodiment of the invention will be described in detail with reference to drawings. FIG. 1 is a schematic diagram illustrating one example of a schematic configuration of a radiographing apparatus according to the present exemplary embodiment. As illustrated in FIG. 1, the radiographing apparatus includes a radiation image detector 101. In addition, the radiographing apparatus may further include a radiation generating device 201.

The radiation image detector 101 converts a radiation image into digital data. The radiation generating device 201 radiates radiations to an object (subject).

The radiation image detector 101 includes a photoelectric conversion unit 102, a control unit 103, a storage unit 104, a correction data update unit 105, and a processing unit 106. The photoelectric conversion unit 102 is configured by having a plurality of light receiving elements two-dimensionally arranged, and formed with amorphous silicon as a main material thereof. The photoelectric conversion unit 102 receives radiations, which are converted into visible light, with the light receiving elements and detects the radiations as a radiation image signal.

The control unit 103 controls the radiographing apparatus. For example, the control unit 103 performs ON/OFF control, control of power supply, and the like of the photoelectric conversion unit 102. Moreover, the control unit 103 acquires radiation image data of the object from the photoelectric conversion unit 102.

In addition, the control unit 103 includes a correction data acquiring unit 130, and the correction data acquiring unit 130 acquires, by image data obtained by photography in a predetermined photographing mode during a non-radiation time of radiations, offset correction data corresponding to the photographing mode. The offset correction data is image data obtained by photography, in a state where no radiation is radiated, in the same photographing mode as that of radiation image data to be a target of offset correction. For example, in a case where the radiation image detector 101 photographs an object in a predetermined photographing mode, image data obtained by photography in this photographing mode in the state where no radiation is radiated becomes offset correction data. The offset correction data is saved in the storage unit 104.

Further, the control unit 103 (correction data acquiring unit 130) includes a first correction data acquiring unit 113 and a second correction data acquiring unit 123.

The first correction data acquiring unit 113 acquires first offset correction data by image data obtained by photography in a first photographing mode. Moreover, the first correction data acquiring unit 113 acquires the predetermined number (first number) of pieces of image data (first image data) in the first photographing mode.

The second correction data acquiring unit 123 acquires second offset correction data by image data obtained by photography in a second photographing mode. Moreover, the second correction data acquiring unit 123 acquires the predetermined number (second number different from the first number) of pieces of image data (second image data) in the second photographing mode.

The storage unit 104 stores therein data such as the radiation image data, the offset correction data, gain correction data, defect correction data, and the like. The gain correction data is image data obtained by photography by radiating radiations, in a state where there is no object, in the same photographing mode as that of radiation image data to be a target of gain correction. For example, in a case where the radiation image detector 101 photographs an object in a predetermined photographing mode, image data obtained by photography by radiating radiations in this photographing mode in the state where there is no object becomes gain correction data. The defect correction data is defect information such as position information of a light receiving element (defect element), which is not able to detect a radiation, in the photoelectric conversion unit 102.

The correction data update unit 105 updates offset correction data (the first offset correction data and the second offset correction data) corresponding to a photographing mode by using the predetermined number of pieces of image data. In this case, the correction data update unit 105 adjusts the number of pieces of image data used for updating the offset correction data, in accordance with the photographing mode.

Moreover, the correction data update unit 105 includes a first correction data update unit 115 and a second correction data update unit 125.

The first correction data update unit 115 updates the first offset correction data corresponding to the first photographing mode by using an average of the predetermined number (first number) of pieces of image data (first image data). In addition, the first correction data update unit 115 may update the first offset correction data corresponding to the first photographing mode the predetermined number (first number) of times by using the image data (first image data) instead of updating the offset correction data by the average of the image data.

The second correction data update unit 125 updates the second offset correction data corresponding to the second photographing mode by using an average of the predetermined number (second number) of pieces of image data (second image data). In addition, the second correction data update unit 125 may update the second offset correction data corresponding to the second photographing mode the predetermined number (second number) of times by using the image data (second image data) instead of updating the offset correction data by the average of the image data.

The processing unit 106 outputs the radiation image data, which is subjected to the offset correction processing, and the like.

Figures 2A, 2B, 2C:
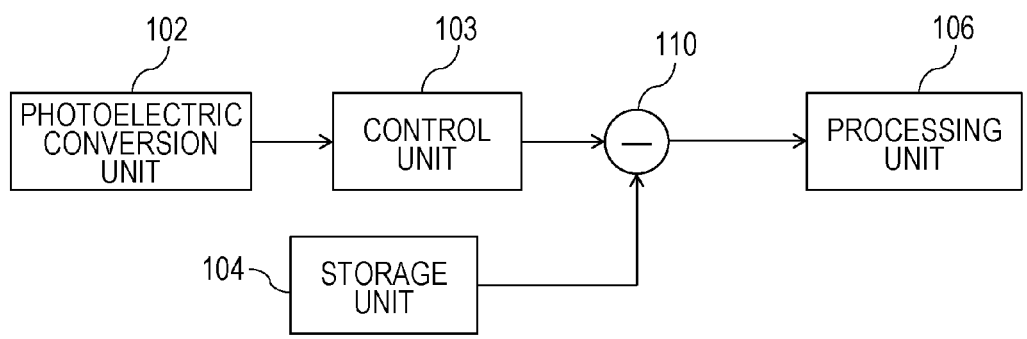
FIGS. 2A to 2C are views for explaining offset correction of the radiographing apparatus according to the first exemplary embodiment.

Next, offset correction of the radiographing apparatus at a time of photography will be described with reference to FIGS. 2A to 2C. FIG. 2A is a schematic diagram illustrating one example of a schematic configuration of the radiographing apparatus at the time of photography. FIG. 2B is a view illustrating one example of radiation image data to be a target of the offset correction. FIG. 2C is a view illustrating one example of offset correction data to be used for the offset correction.

When capturing a radiation image of an object, the photoelectric conversion unit 102 detects a radiation image signal (radiation image data) which is converted into visible light. The control unit 103 acquires the radiation image data of the object from the photoelectric conversion unit 102. A subtracter 110 subtracts offset correction data from the radiation image data, and outputs the resultant to the processing unit 106. Moreover, in a case where radiation images are photographed in a plurality of photographing modes, the subtracter 110 subtracts offset correction data corresponding to each of the photographing modes from radiation image data obtained by photography in each of the photographing modes, and outputs the resultant to the processing unit 106. The processing unit 106 outputs the radiation image data subjected to the offset correction processing.

In this case, before photographing the object, the radiation image detector 101 acquires the offset correction data for each of the plurality of photographing modes which are different in an accumulation time, an amplification factor of an amplifier, binning of pixels, or the like. The first correction data acquiring unit 113 acquires the first offset correction data by the image data obtained by photography in the first photographing mode. The second correction data acquiring unit 123 acquires the second offset correction data by the image data obtained by photography in the second photographing mode. The offset correction data corresponding to each of the photographing modes is saved in the storage unit 104.

In a case where a radiation image is photographed in each of photographing modes of MODE1 to MODE4, the first correction data acquiring unit 113 acquires offset correction data W1 (first offset correction data) by image data obtained by photography in MODE1 (first photographing mode). The second correction data acquiring unit 123 acquires offset correction data W2 (second offset correction data) by image data obtained by photography in MODE2 (second photographing mode).

Note that, the first correction data update unit 115 may set, as an initial value of the offset correction data W1, average data obtained by averaging a plurality (first number) of pieces of image data obtained by photography in MODE1. The second correction data update unit 125 may set, as an initial value of the offset correction data W2, average data obtained by averaging a plurality (second number) of pieces of image data obtained by photography in MODE2 (second photographing mode).

When update of the offset correction data of MODE1 and MODE2 is completed, similarly to the above, the first correction data acquiring unit 113 or the second correction data acquiring unit 123 acquires offset correction data W3 by image data obtained by photography in MODE3. Moreover, the first correction data acquiring unit 113 or the second correction data acquiring unit 123 acquires offset correction data W4 by image data obtained by photography in MODE4.

The subtracter 110 respectively subtracts offset correction data W1 to W4 corresponding to MODE1 to MODE4 from radiation images X1 to X4 captured in MODE1 to MODE4, and outputs the resultant to the processing unit 106. The processing unit 106 outputs radiation images X1-W1, X2-W2, X3-W3, and X4-W4 which are subjected to the offset correction processing.

Figures 3A, 3B, 3C:
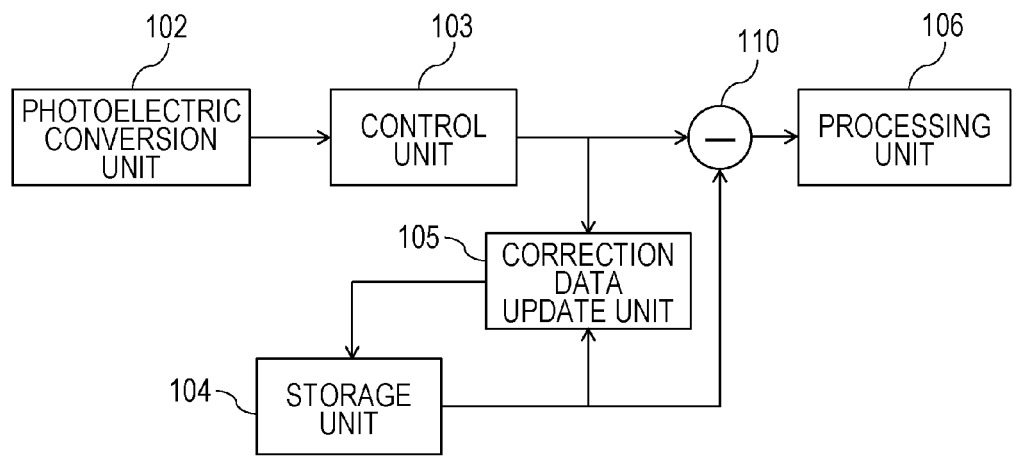
FIGS. 3A to 3C are views for explaining update of offset correction data of the radiographing apparatus according to the first exemplary embodiment.

Next, update of offset correction data will be described with reference to FIGS. 3A to 3C. FIG. 3A is a schematic diagram illustrating one example of a schematic configuration of the radiographing apparatus in the update of the offset correction data. FIG. 3B is a view illustrating one example of the latest image data to be used for the update of the offset correction data. FIG. 3C is a view illustrating one example of the offset correction data before the update.

In a time other than a time of capturing a radiation image of an object, the photoelectric conversion unit 102 detects an image signal (image data) obtained by photography in a state where no radiation is radiated. The control unit 103 (correction data acquiring unit 130) acquires the image data obtained by photography performed during a non-radiation time of radiations.

The correction data update unit 105 inputs image data which is newly generated (latest image data) from the control unit 103 (correction data acquiring unit 130), and updates offset correction data, which is saved in the storage unit 104, by using the latest image data. The offset correction data is updated, and offset correction of a radiation image is thereby performed by using the latest offset correction data, thus making it possible to suppress noise which increases over time and improve an image quality of the radiation image.

In a case where radiation images are captured in a plurality of photographing modes, the correction data update unit 105 respectively updates offset correction data corresponding to each of the photographing modes. The updated offset correction data is saved in the storage unit 104.

In addition, the correction data update unit 105 adjusts the number of pieces of image data, which is used for updating the offset correction data, based on a noise factor of the offset correction data. The correction data update unit 105 adjusts the number of pieces of image data, which is used for updating the offset correction data, based on, for example, at least one of an accumulation time of a photographing mode, an amplification factor of an amplifier, and binning of pixels.

Since an influence of noise is small in a photographing mode in which a gain is low, the number of pieces of image data is set to be smaller than that of a photographing mode in which the gain is high. In the present exemplary embodiment, the number (first number) of pieces of image data is set as 5 in a photographing mode in which the gain is lower than a predetermined threshold (MODE1), and the number (second number) of pieces of image data is set as 20 in a photographing mode in which the gain is higher than the predetermined threshold (MODE2). In this manner, the first correction data update unit 115 sets the number of pieces of image data to be smaller in the photographing mode, in which the gain is less than the predetermined threshold, than that of the photographing mode in which the gain is equal to or more than the predetermined threshold.

Further, since the influence of noise is small in a photographing mode in which a frame rate is low, the number of pieces of image data is set to be smaller than that of a photographing mode in which the frame rate is high. In the present exemplary embodiment, the number (first number) of pieces of image data is set as 5 in a photographing mode in which the frame rate is lower than a predetermined threshold (MODE1), and the number (second number) of pieces of image data is set as 20 in a photographing mode in which the frame rate is higher than the predetermined threshold (MODE2). In this manner, the first correction data update unit 115 sets the number of pieces of image data to be smaller in the photographing mode, in which the frame rate is less than the predetermined threshold, than that of the photographing mode in which the frame rate is equal to or more than the predetermined threshold.

In a case where radiation images are captured in the photographing modes of MODE1 to MODE4, the first correction data update unit 115 updates the offset correction data W1 corresponding to MODE1 by using an average of five (the first number of) pieces of image data (first image data). The second correction data update unit 125 updates the offset correction data W2 corresponding to MODE2 by using an average of twenty (the second number of) pieces of image data (second image data). That is, the first offset correction data is updated by using the first number of pieces of image data, and the second offset correction data is updated by using the second number of pieces of image data.

For example, in a case where the offset correction data W1 is updated by using the average of the image data, the first correction data acquiring unit 113 acquires five pieces of the latest image data (offset correction data) I1 $I1_{f=1}$, $I1_{f=2}$, $I1_{f=3}$, $I1_{f=4}$, and $I1_{f=5}$) which are obtained by photography in MODE1 during a non-radiation time of radiations. The first correction data update unit 115 substitutes an average of the five pieces of the latest image data I1 "($I1_{f=1}+I1_{f=2}+I1_{f=3}+I1_{f=4}+I1_{f=5}$)/5" for the first offset correction data W1, and thereby updates the offset correction data. In this case, f is an acquisition number of the latest image data I1.

Note that, in a case where the offset correction data is updated by substituting the average of the image data for the offset correction data, it is possible to efficiently reduce noise compared with the case of substituting one piece of image data for the offset correction data.

Moreover, instead of substituting the average of the image data for the offset correction data, the first correction data update unit 115 may update the offset correction data W1 corresponding to MODE1 five times (the first number of times) by using one piece of the latest image data (first image data). The second correction data update unit 125 may update the offset correction data W2 corresponding to MODE2 twenty times (the second number of times) by using one piece of the latest image data (second image data).

Also in this case, the first offset correction data is updated by using the first number of pieces of image data, and the second offset correction data is updated by using the second number of pieces of image data.

Here, the numbers of pieces of image date used for updating the offset correction data are different in at least one pair of the offset correction data W1 to W4. For example, the number (first number) of pieces of image data used for updating the offset correction data W1 (first offset correction data) is different from the number (second number) of pieces of image date used for updating the offset correction data W2 (second offset correction data).

In addition, the number (first number) of pieces of image data used for updating the offset correction data W1 only needs to be the same as the number (first number) of pieces of image data used for calculating the initial value of the offset correction data W1. The number (second number) of pieces of image data used for updating the offset correction data W2 only needs to be the same as the number (second number) of pieces of image data used for calculating the initial value of the offset correction data W2.

In the case of updating the offset correction data W1 five (the first number of) times by using one piece of the latest image data, the first correction data acquiring unit 113 acquires the latest image data (offset correction data) I1 obtained by photography in MODE1 during the non-radiation time of radiations. The first correction data update unit 115 updates the offset correction data W1 (first offset correction data) by using the latest image data I1. For example, the first correction data update unit 115 updates the offset correction data W1 by weighted average data obtained by weighting and averaging the latest image data I1 and the offset correction data W1, and performs this update five (the first number of) times.

In this case, offset correction data $W1_{n=0}$ is updated to offset correction data $W1_{n=1}$ by weighted average data obtained by weighting and averaging the latest image data $I1_{f=1}$ and the offset correction data $W1_{n=0}$, and the offset correction data $W1_{n=1}$ is updated to offset correction data $W1_{n=2}$ by weighted average data obtained by weighting and averaging the latest image data $I1_{f=2}$ and the offset correction data $W1_{n=1}$.

Then, the offset correction data $W1_{n=2}$ is updated to offset correction data $W1_{n=3}$ by weighted average data obtained by weighting and averaging the latest image data $I1_{f=3}$ and the offset correction data $W1_{n=2}$, and the offset correction data $W1_{n=3}$ is updated to offset correction data $W1_{n=4}$ by weighted average data obtained by weighting and averaging the latest image data $I1_{f=4}$ and the offset correction data $W1_{n=3}$.

Further, the offset correction data $W1_{=4}$ is updated to offset correction data $W1_{n=5}$ by weighted average data obtained by weighting and averaging the latest image data $I1_{f=5}$ and the offset correction data $W1_{n=4}$, and the five-time update is completed. Here, f is an acquisition number of the latest image data I1, and n is the number of times of update of the offset correction data W1.

After the offset correction data W1 is updated five times, similarly to the above, the second correction data update unit 125 updates the offset correction data W2 twenty (the second number of) times by using the latest image data. Moreover, after the offset correction data W2 is updated twenty times, the offset correction data W3 is updated, and after the offset correction data W3 is updated, the offset correction data W4 is updated.

Then, after the offset correction data W4 is updated, the offset correction data W1 is updated again. In this manner, the first correction data update unit 115 updates the offset correction data W1 (first offset correction data) the first number of times of update again after the second correction data update unit 125 updates the offset correction data W2 (second offset correction data).

Figure 4:
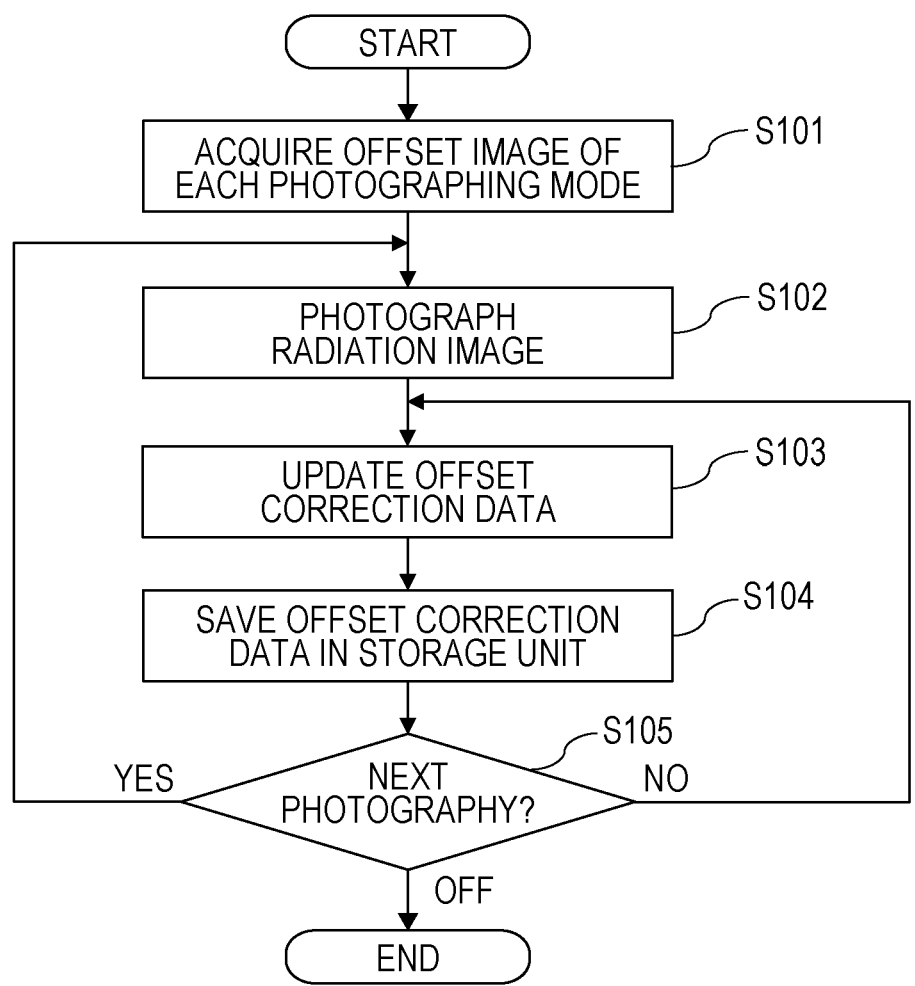
FIG. 4 is a flowchart illustrating one example of an operation of the radiographing apparatus according to the first exemplary embodiment.

Next, an operation of the radiographing apparatus will be described with reference to FIG. 4. When power is supplied to the radiographing apparatus, the correction data acquiring unit 130 acquires offset correction data of each photographing mode (step S101). The first correction data acquiring unit 113 acquires the offset correction data W1 by image data obtained by photography in MODE1 (first photographing mode). Moreover, after the photographing mode is switched, the second correction data acquiring unit 123 acquires the offset correction data W2 by image data obtained by photography in MODE2 (second photographing mode).

The first correction data update unit 115 sets, as the initial value of the offset correction data W1, image data (offset correction data) which is acquired after power is supplied to the radiographing apparatus. The initial value of the offset correction data may be one piece of image data obtained by photography in MODE1 during the non-radiation time of radiations, or may be average data obtained by averaging a plurality of pieces of image data obtained by photography in MODE1 during the non-radiation time of radiations. Similarly, initial values of the offset correction data W2 to W4 in MODE2 to MODE4 are set.

After the offset correction data is acquired, the radiographing apparatus captures a radiation image of an object (subject) (step S102). The radiation image of the object is corrected by offset correction processing, and output from the processing unit 106. In the offset correction processing, the offset correction data corresponding to each photographing mode is subtracted from radiation image data. In a case where the photographing mode is switched, offset correction data is also switched in accordance with the photographing mode.

In a time when a radiation image is not captured (non-radiation time of radiations), the correction data update unit 105 updates the offset correction data corresponding to each photographing mode by using the predetermined number of pieces of image data (step S103). The number of pieces of image data is adjusted based on at least one of an accumulation time, an amplification factor of an amplifier, and binning of pixels.

For example, since the influence of noise is small in a photographing mode in which the gain is low, the number of pieces of image data used for update is set to be smaller than that of a photographing mode in which the gain is high. In the present exemplary embodiment, the number (first number) of pieces of image data is set as 5 in a photographing mode in which the gain is lower than a predetermined threshold (MODE1), and the number (second number) of pieces of image data is set as 20 in a photographing mode in which the gain is higher than the predetermined threshold (MODE2).

The first correction data update unit 115 updates the offset correction data W1 corresponding to MODE1 (first photographing mode) by using an average of the first number of (five) pieces of image data. Moreover, the first correction data update unit 115 may update the offset correction data W1 corresponding to MODE1 (first photographing mode) the first number of (five) times by using the image data.

The second correction data update unit 125 updates the offset correction data W2 corresponding to MODE2 (second photographing mode) by using an average of the second number of (twenty) pieces of image data. Moreover, the second correction data update unit 125 may update the offset correction data W2 corresponding to MODE2 (second photographing mode) the second number of (twenty) times by using the image data.

The updated offset correction data is saved in the storage unit 104 for each photographing mode (step S104).

In a case where a capturing request of a next radiation image is input at step S105, the procedure returns to step S102, and the radiation image of the object is corrected by the offset correction processing and outputs from the processing unit 106. In the offset correction processing, offset correction data corresponding to each photographing mode is subtracted from the radiation image data by using the updated offset correction data.

After the radiographing apparatus captures the radiation image of the object in the predetermined photographing mode at step S102, the numbers (the first number and the second number) of pieces of image data used for updating the offset correction data may be reset. In this case, the first correction data acquiring unit 113 acquires the first number of pieces of image data (first image data) after the radiographing apparatus captures the radiation image of the object in MODE1 (first photographing mode). The first correction data update unit 115 updates the offset correction data W1 by using the first number of pieces of image data.

The second correction data acquiring unit 123 acquires the second number of pieces of image data (second image data) after the radiographing apparatus captures the radiation image of the object in MODE2 (second photographing mode). The second correction data update unit 125 updates the offset correction data W2 by using the second number of pieces of image data.

In a case where the capturing request of the next radiation image is not input at step S105, the procedure returns to step S103, and update of the offset correction data corresponding to each photographing mode is iterated until the capturing request of the next radiation image is input. For example, the offset correction data W1 is updated again after the offset correction data W1 to W4 is updated.

According to the present exemplary embodiment, by adjusting the numbers (the first number and the second number) of pieces of image data used for updating offset correction data in accordance with a photographing mode, it is possible to update the offset correction data by using the appropriate number of pieces of image data in accordance with each photographing mode. As a result thereof, improvement of an image quality of a radiation image is achieved, and it becomes unnecessary to acquire unnecessary image data, so that it is possible to shorten a waiting time of the radiation image detector 101.

Second Exemplary Embodiment

Next, one example of a second exemplary embodiment of the invention will be described in detail with reference to drawings. Note that, description of a configuration, a function, and an operation which are similar to those of the aforementioned exemplary embodiment will be omitted, and difference from the present exemplary embodiment will be mainly described.

Figures 5A, 5B, 5C:
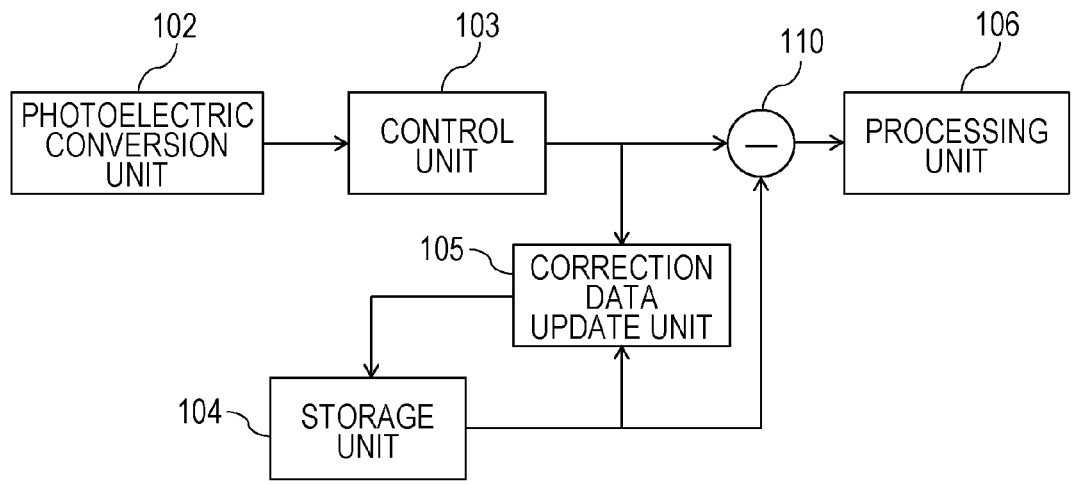
FIGS. 5A to 5C are views for explaining update of offset correction data of a radiographing apparatus according to a second exemplary embodiment.

FIG. 5A is a schematic diagram illustrating one example of a schematic configuration of the radiographing apparatus in update of offset correction data. FIG. 5B is a view illustrating one example of the latest image data used for the update of the offset correction data. FIG. 5C is a view illustrating one example of offset correction data before the update and after the update.

In the second exemplary embodiment, the first correction data update unit 115 updates the first offset correction data corresponding to the first photographing mode the predetermined number (first number) of times of update, by using image data (first image data). Moreover, the second correction data update unit 125 updates the second offset correction data corresponding to the second photographing mode the predetermined number (second number) of times of update, by using image data (second image data).

In this case, the number (first number) of pieces of image data used for updating the offset correction data W1 only needs to be the same as the number (first number) of pieces of image data used for calculating the initial value of the offset correction data W1. Moreover, the number (second number) of pieces of image data used for updating the offset correction data W2 only needs to be the same as the number (second number) of pieces of image data used for calculating the initial value of the offset correction data W2.

The first correction data update unit 115 generates first offset correction data $W1_n$ (value of the first offset correction data in n-th update) by using weighted average data obtained by weighting and averaging the latest image data $I1_n$ (value of the latest first image data in n-th update) and offset correction data $W1_m$ (value of the first offset correction data in "m=n−1"-th update). The offset correction data $W1_m$ is updated by the offset correction data $W1_n$.

The second correction data update unit 125 generates second offset correction data $W2_n$ (value of the second offset correction data in n-th update) by using weighted average data obtained by weighting and averaging the latest image data $I2_n$ (value of the latest second image data in n-th update) and offset correction data $W2_m$ (value of the second offset correction data in "m=n−1"-th update). The offset correction data $W2_m$ is updated by the offset correction data $W2_n$.

Similarly, offset correction data $W3_m$ is updated by offset correction data $W3_n$ by using weighted average data obtained by weighting and averaging the latest image data $I3_n$ and the offset correction data $W3_m$. Moreover, offset correction data $W4_m$ is updated by offset correction data $W4_n$ by using weighted average data obtained by weighting and averaging the latest image data $I4_n$ and the offset correction data $W4_m$.

Though any weighting factor of weighting and averaging may be used, in the present exemplary embodiment, the first correction data update unit 115 calculates the offset correction data $W1_n$ corresponding to a photographing mode by a following formula (1).

$$W_n = W_m \cdot (k-1)/k + I_n/k \qquad (1)$$

n: the number of times of update (integer equal to or more than 1)
$W_n$: a value of the first offset correction data in n-th update
$W_m$: a value of the first offset correction data in "m=n−1"-th update (m is an integer equal to or more than 0)
$W_{n=0}$: an initial value of the first offset correction data
k: an integer equal to or more than 2 (first number)
$I_n$: a value of the latest first image data in n-th update Similarly, the second correction data update unit 125 may calculate the offset correction data $W2_n$ corresponding to a photographing mode by the formula (1). In this case, k is the second number. That is, the correction data update unit 105 multiplies the offset correction data $W_m$ by a weighting factor (k−1)/k and multiplies the latest image data $I_n$ by a weighting factor 1/k, and thereby generates the offset correction data $W_n$ for each photographing mode. Then, the offset correction data $W_m$ is updated by the offset correction data W.

In a case where the offset correction data W1 is updated five (the first number of) times by using one piece of the latest image data, the first correction data acquiring unit 113 acquires the latest image data $I1_{n=1}$ obtained by photography in MODE1 during the non-radiation time of radiations, and outputs it to the first correction data update unit 115. The first correction data update unit 115 updates offset correction data $W1_{m=0}$ to offset correction data $W1_{n=1}$ by weighted average data obtained by weighting and averaging the latest image data $I1_{n=1}$ and the offset correction data $W1_{m=0}$. The first correction data update unit 115 performs this update five (the first number of) times, and performs update from the offset correction data $W1_{m=0}$ to offset correction data $W1_{n=5}$.

In a case where the offset correction data W2 is updated twenty (the second number of) times by using one piece of the latest image data, the second correction data acquiring unit 123 acquires the latest image data $I2_{n=1}$ obtained by photography in MODE2 during the non-radiation time of radiations, and outputs it to the second correction data update unit 125. The second correction data update unit 125 updates offset correction data $W2_{m=0}$ to offset correction data $W2_{n=1}$ by weighted average data obtained by weighting and averaging the latest image data $I2_{n=1}$ and the offset correction data $W2_{m=0}$. The second correction data update unit 125 performs this update twenty (the second number of) times, and performs update from the offset correction data $W2_{m=0}$ to offset correction data $W2_{n=20}$.

Note that, the first correction data update unit 115 may update the offset correction data W1 by using an average of five (the first number of) pieces of the first image data every five (the first number of) times of update. In this case, the first correction data update unit 115 performs update from the offset correction data $W1_{m=0}$ to offset correction data $W1_{n=4}$ according to the formula (1) up to n=4-th update. The first correction data update unit 115 updates the offset correction data $W1_{n=4}$ to the offset correction data $W1_{n=5}$ by using an average of five (the first number of) pieces of the latest image data $I1_{n=1}$ to $I1_{n=5}$ (first image data) in n=5-th update.

Similarly, the first correction data update unit 115 updates offset correction data $W1_{n=9}$ to offset correction data $W1_{n=10}$ by using an average of five (the first number of) pieces of the latest image data $I1_{n=6}$ to $I1_{n=10}$ (first image data) in n=10-th update.

Moreover, the second correction data update unit 125 may update the offset correction data W2 by using an average of twenty (the second number of) pieces of the second image data every twenty (the second number of) times of update. In this case, the second correction data update unit 125 performs update from the offset correction data $W2_{m=0}$ to offset correction data $W2_{n=19}$ according to the formula (1) up to n=19-th update. The second correction data update unit 125 updates the offset correction data $W2_{n=19}$ to the offset correction data $W2_{n=20}$ by using an average of twenty (the second number of) pieces of the latest image data $I2_{n=1}$ to $I2_{n=20}$ (second image data) in n=20-th update.

Similarly, the second correction data update unit 125 updates offset correction data $W2_{n=39}$ to offset correction data $W2_{n=40}$ by using an average of twenty (the second number of) pieces of the latest image data $I2_{n=21}$ to $I2_{n=40}$ (second image data) in n=40-th update.

According to the present exemplary embodiment, even in a case where the latest image data is not appropriate as offset correction data, it is possible to reduce an influence in a quality of the latest image data by weighting and averaging the latest image data and offset correction data.

Moreover, it is possible to generate appropriate offset correction data by multiplying the offset correction data $W_m$ by a weighting factor of weighting and averaging (k−1)/k and multiplying the image data $I_n$ by a weighting factor 1/k.

In addition, by updating offset correction data by using an average of a plurality of pieces of the latest image data every predetermined number of times of update, it is possible to perform offset correction with appropriate offset correction data, thus making it possible to efficiently reduce noise.

Though the exemplary embodiments according to the invention have been described as above, the invention in not limited thereto, and any change and modification can be made within the scope described in claims.

The invention is able to be realized by processing in which a program which realizes one or more functions of the above-described exemplary embodiments is supplied to a system or an apparatus via a network or a computer readable storage medium and one or more processors of a computer in the system or the apparatus reads and executes the program. Moreover, the invention is able to be realized also by a circuit which realizes one or more functions (for example, an ASIC).

In addition, the radiographing apparatus may include a counter which counts the number of times of update by the first correction data update unit 115. The counter may reset the number of times of update as 0 every predetermined number (first number) of times of update, and perform counting the same number (first number) of times of update again. Further, the counter may reset the number of times of update as 0 after the radiographing apparatus captures a radiation image of an object in the first photographing mode, and perform counting the same number (first number) of times of update again.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2015-100412, filed on May 15, 2015, which is hereby incorporated by reference herein in its entirety.

What is claimed is:

1. A radiation image detector comprising:
a correction data acquiring unit configured to acquire, by image data obtained by photography in a predetermined photographing mode, offset correction data corresponding to the photographing mode; and
a correction data update unit configured to update the offset correction data corresponding to the photographing mode by using a predetermined number of pieces of the image data, and configured to adjust the number of pieces of the image data according to the photographing mode such that a waiting time from photography detection of a radiation image by the radiation image detector to a next photography is shortened.

2. A radiographing apparatus comprising:
a processor and a storage medium performing as function for:
a correction data acquiring unit configured to acquire, by image data obtained by photography in a predetermined photographing mode, offset correction data corresponding to the photographing mode, wherein the correction data acquiring unit includes:
a first correction data acquiring unit configured to acquire a first number of pieces of first image data in a first photographing mode, and
a second correction data acquiring unit configured to acquire a second number of pieces of second image data, which is different from the first number, in a second photographing mode, and
a correction data update unit configured to update the offset correction data corresponding to the photographing mode by using a predetermined number of pieces of the image data, and configured to adjust the number of pieces of the image data according to the photographing mode, wherein the correction data update unit includes:
a first correction data update unit configured to update first offset correction data corresponding to the first photographing mode by using an average of the first number of pieces of the first image data, and
a second correction data update unit configured to update second offset correction data corresponding to the second photographing mode by using an average of the second number of pieces of the second image data.

3. The radiographing apparatus according to claim 2, wherein the first correction data acquiring unit acquires the first number of pieces of the first image data after the radiographing apparatus captures a radiation image of an object in the first photographing mode.

4. The radiographing apparatus according to claim 2, wherein the first correction data update unit sets, as an initial value of the first offset correction data, average data obtained by averaging the first number of pieces of the first image data after power is supplied to the radiographing apparatus.

5. A radiographing apparatus comprising:
a processor and a storage medium performing as function for:
a correction data acquiring unit configured to acquire, by image data obtained by photography in a predetermined photographing mode, offset correction data corresponding to the photographing mode, wherein the correction data acquiring unit includes:
a first correction data acquiring unit configured to acquire a first number of pieces of first image data in a first photographing mode, and
a second correction data acquiring unit configured to acquire a second number of pieces of second image data, which is different from the first number, in a second photographing mode, and
a correction data update unit configured to update the offset correction data corresponding to the photographing mode by using a predetermined number of pieces of the image data, and configured to adjust the number of pieces of the image data according to the photographing mode, wherein the correction data update unit includes a first correction data update unit configured to update first offset correction data corresponding to the first photographing mode a first number of times by using the first image data, and
a second correction data update unit configured to update second offset correction data corresponding to the second photographing mode a second number of times by using the second image data.

6. The radiographing apparatus according to claim 5, wherein the first correction data update unit updates the first offset correction data by using weighted average data obtained by weighting and averaging a latest first image data and the first offset correction data.

7. The radiographing apparatus according to claim 6, wherein the first correction data update unit calculates the first offset correction data by a following formula:

$$W_n = W_m \cdot (k-1)/k + I_n/k,$$

wherein
n is the number of times of update (integer equal to or more than 1),
$W_n$ is a value of the first offset correction data in n-th update,
$W_m$ is a value of the first offset correction data in "m=n−1"-th update (m is an integer equal to or more than 0),
$W_m = 0$ is an initial value of the first offset correction data,
k is an integer equal to or more than 2 (first number), and
$I_n$ is a value of the latest first image data in n-th update.

8. The radiographing apparatus according to claim 5, wherein the first correction data update unit updates the first offset correction data every first number of times of update by using an average of the first number of pieces of the first image data.

9. A radiographing apparatus comprising:
a processor and a storage medium performing as function for:
a correction data acquiring unit configured to acquire, by image data obtained by photography in a predetermined photographing mode, offset correction data corresponding to the photographing mode, and
a correction data update unit configured to update the offset correction data corresponding to the photographing mode by using a predetermined number of pieces of the image data, and configured to adjust the number of pieces of the image data according to the photographing mode,
wherein, in a photographing mode in which a gain is less than a predetermined threshold, the correction data update unit sets the number of pieces of the image data to be smaller than that of a photographing mode in which the gain is equal to or more than the predetermined threshold.

10. A radiographing apparatus comprising:
a processor and a storage medium performing as function for:
a correction data acquiring unit configured to acquire, by image data obtained by photography in a predetermined photographing mode, offset correction data corresponding to the photographing mode, and
a correction data update unit configured to update the offset correction data corresponding to the photographing mode by using a predetermined number of pieces of the image data, and configured to adjust the number of pieces of the image data according to the photographing mode,
wherein, in a photographing mode in which a frame rate is less than a predetermined threshold, the correction data update unit sets the number of pieces of the image data to be smaller than that of a photographing mode in which the frame rate is equal to or more than the predetermined threshold.

11. A controlling method for a radiographing apparatus, the controlling method comprising:
acquiring, by image data obtained by photography in a predetermined photographing mode, offset correction data corresponding to the photographing mode, wherein acquiring includes:
acquiring, as a first correction data acquiring, a first number of pieces of first image data in a first photographing mode, and
acquiring, as a second correction data acquiring, a second number of pieces of second image data, which is different from the first number, in a second photographing mode; and
updating the offset correction data corresponding to the photographing mode by using a predetermined number of pieces of the image data, and adjusting the number of pieces of the image data according to the photographing mode, wherein updating includes:
updating, as a first correction data update, first offset correction data corresponding to the first photographing mode by using an average of the first number of pieces of the first image data, and
updating, as a second correction data update, second offset correction data corresponding to the second photographing mode by using an average of the second number of pieces of the second image data.

12. A non-transitory computer-readable storage medium storing a program for causing a computer to execute a controlling method for a radiographing apparatus, the controlling method comprising:
acquiring, by image data obtained by photography in a predetermined photographing mode, offset correction data corresponding to the photographing mode, wherein acquiring includes:
acquiring, as a first correction data acquiring, a first number of pieces of first image data in a first photographing mode, and
acquiring, as a second correction data acquiring, a second number of pieces of second image data, which is different from the first number, in a second photographing mode; and
updating the offset correction data corresponding to the photographing mode by using a predetermined number of pieces of the image data, and adjusting the number of pieces of the image data according to the photographing mode, wherein updating includes:
updating, as a first correction data update, first offset correction data corresponding to the first photographing mode by using an average of the first number of pieces of the first image data, and
updating, as a second correction data update, second offset correction data corresponding to the second photographing mode by using an average of the second number of pieces of the second image data.

* * * * *